United States Patent [19]

Tennigkeit et al.

[11] Patent Number: 5,053,051
[45] Date of Patent: Oct. 1, 1991

[54] MEANS AND METHOD FOR THE OXIDATIVE DYEING, ESPECIALLY THE REDYEING, OF LIVING HAIR: MICRO-ENCAPSULATED ACID

[75] Inventors: Jürgen Tennigkeit, Seeheim; Herbert Lorenz, Gross-Bieberau, both of Fed. Rep. of Germany; Hirotsugu Segawa, Osaka, Japan

[73] Assignee: Goldwell GmbH, Darmstadt-Eberstadt, Fed. Rep. of Germany

[21] Appl. No.: 411,465

[22] PCT Filed: Dec. 19, 1988

[86] PCT No.: PCT/EP88/01177

§ 371 Date: Sep. 21, 1989

§ 102(e) Date: Sep. 21, 1989

[87] PCT Pub. No.: WO89/06531

PCT Pub. Date: Jul. 27, 1989

[30] Foreign Application Priority Data

Jan. 21, 1988 [DE] Fed. Rep. of Germany ....... 3801606

[51] Int. Cl.$^5$ .................... A61K 7/13; B01J 13/02; D06P 3/08
[52] U.S. Cl. ............................ 8/406; 8/405; 8/429; 8/431; 8/557; 8/594; 8/599
[58] Field of Search .................................. 8/406, 429

[56] References Cited

U.S. PATENT DOCUMENTS

| | | | |
|---|---|---|---|
| 3,975,515 | 8/1976 | Wajaroff et al. | 8/405 |
| 4,020,850 | 11/1986 | Bachmann et al. | 8/406 |
| 4,425,132 | 1/1984 | Grollier et al. | 8/405 |
| 4,844,711 | 7/1989 | Hoppe et al. | 8/406 |

FOREIGN PATENT DOCUMENTS 1295038 11/1972 United Kingdom .

*Primary Examiner*—A. Lionel Clingman

[57] ABSTRACT

A mixture for the oxidative dyeing of human or animal hair, which is prepared immediately before application by mixing an oxidant and a dye base in cream, gel or powder form containing at least one oxidative dye and adjusting to a pH in the range of 8.0 to 10.5.

The means contains in the freshly-prepared state a microencapsulated, acid-reacting compound in an amount which shifts the pH of the dye into the weakly alkaline (pH$\leq$8), neutral or acid range.

The encapsulating material for the acid-reacting compound is soluble in the alkaline dye or changeable at least in its strength properties in the sense of a weakening, the wall thickness of the microcapsules being so adjusted that the walls are dissolved or weakened within a period between 10 and 60 minutes to such an extent that the acid-reacting compound is able by itself or upon the exertion of an additional mechanical stress to emerge into the dye.

Furthermore, the invention relates to the use of the means for the redyeing of dyed hair.

9 Claims, No Drawings

MEANS AND METHOD FOR THE OXIDATIVE DYEING, ESPECIALLY THE REDYEING, OF LIVING HAIR: MICRO-ENCAPSULATED ACID

The invention relates to a mixture for the oxidative dyeing of human or animal hair, which is prepared immediately before application by mixing an oxidant and a dye base in cream, gel or powder form containing at least one oxidation dye, and is adjusted to a pH value in the range from 8.0 to 10.5, and to a method for the redyeing of dyed hair, in which a hair dye which in the ready-to-use state has a pH value in the range between 8.0 to 10.5 is prepared from an oxidant and a dye base in powder, cream or gel form containing at least one oxidation dye, which then is applied to the regrowth of the hair that is to be redyed and made to act thereon for a given period of time, and then is combed into the already-dyed hair lengths and ends where it is made to act for an additional given period of time, and lastly is washed out.

For the enduring coloration of human hair, alkaline dye bases containing at least one oxidative dye are used in cream, gel or powder form, which are mixed immediately before application with an acid oxidant, e.g., hydrogen peroxide or an emulsion containing hydrogen peroxide, to form the ready-to-use hair dye for application to the hair. The coloring is produced in this case by the reaction of specific developer substances with specific coupler substances in the presence of a suitable oxidant. The ready-to-use preparation is decidedly in the alkaline range, so that the surfaces of the hairs to be dyed are opened up in a manner advantageous for the penetration of the oxidation dyes. On the other hand, alkaline preparations also affect the hair so that, especially in the case of repeated actions, e.g., repeated redyeing, they can cause harm to the hair. Such redyeing, however, is necessary in order to match the color of the undyed hair regrowth to the already-dyed hair lengths, in which case, as a rule, the previously dyed hair lengths must also be color-refreshed if they have faded from the original color in the course of time due to external factors such as solar radiation, frequent washing, and the like.

The invention is addressed to the problem of finding a hair dye as well as a method for the preparation and subsequent application of the dye to the hair that is to be treated, which will not lead to the above-described hair damage, even after repeated redyeing.

The hair dye prepared from an oxidant and a dye base in cream, gel or powder form containing at least one oxidative dye, in accordance with the invention is characterized by the fact that, in the freshly prepared state, it contains a microencapsulated, acid-reacting compound in an amount which shifts the pH of the hair dye into the neutral, weakly alkaline (pH$\leq$8) or weakly acid range, and that the encapsulating material for the acid-reacting compound is soluble in the alkaline dye or at least is variable in its strength properties in the sense of weakening them, the wall thickness of the microcapsules being so adjusted that within a period of time between 10 and 60 minutes they are dissolved or weakened to the extent that the acid-reacting compound can emerge into the dye by itself or upon the exercise of an additional mechanical stress.

The acid-reacting compound is, for example, an acrylic resin containing carboxyl groups (Rohagit S) or it is an acid such as citric acid, tartaric acid or malic acid, which when mixed with the alkaline dye produces a color change in addition to the pH shift or contains an indicator which causes such a color change.

Also advantageous is the use or concomitant use of ascorbic acid as the acid-reacting compound, because, in addition to the shifting of the pH of the dye towards neutrality or acidity—which is delayed with respect to the above-mentioned acid-reacting compounds—also has a reducing action on the hydrogen peroxide contained as oxidant in the prepared hair dye. In the reducing reaction (redox effect) exothermic heat is produced, which results in an acceleration of the dyeing process. The addition of the encapsulated ascorbic acid thus produces a delayed shift of the pH value, a reduction of the hydrogen peroxide content, a warming of the dye composition, and thus a shortening of the time of action.

In the case of the redyeing of dyed hair, the procedure is that, in a known manner, a hair dye is prepared from an oxidant and a dye base in cream, gel or powder form containing at least one oxidant, and has, in the ready-to-use state, a pH in the range between 8.0 and 10.5, and it is then applied to the regrowth of the hair and there made to act for a given period of time, and then it is combed through into the already-dyed hair lengths and ends and there made to act for an additional given period of time, and finally it is washed out, while in a further development in accordance with the invention, an acid-reacting compound in microencapsulated form is added during the preparation of the dye, in such an amount that the pH of the dye, when mixed with this acid-reacting compound, is barely shifted into the weakly alkaline (pH$\leq$8), neutral, or slightly acid range, while the wall thickness of the microcapsules soluble in the alkaline dye or variable in the sense of a weakening of their strength properties is selected such that the acid-reacting compound contained in the microcapsules emerges into the dye within a period of time between 10 and 60 minutes. Combing the dye into the hair lengths and ends promotes the rupture of incompletely dissolved or weakened microcapsules as well as the transfer of the acid-reacting compound to the dye and its intimate mixing therewith.

If the above-mentioned acrylic resin containing carboxyl groups is used as the acid-reacting compound, entry into the until then alkaline dye is also indicated by a color change, which signals that the pH of the dye applied up to now only to the regrowth has become lower and it can be combed into the body of the hair and to the ends for the purpose of freshening the color in these parts of the hair, with a reduced pH and therefore in a form which will give rise to no further damage.

The preparation of the hair dye can be performed by mixing together the dye base, the oxidant and the microencapsulated acid-reacting composition from stocks kept separately on hand before the dye is prepared for application.

Alternatively, however, the oxidant and the microencapsulated acid-reacting compound can be premixed with the dye base in the required ratio. The acid-reacting microencapsulated compound can be premixed with the oxidant because the acid oxidant does not attack the material of the microcapsules, so that this premixing can be performed by the manufacturer, and the assurance will be had in every case that the correct ratio of the amounts of oxidants and acid-reacting compound is established. Instead of the one acid-reacting compound mentioned, two or more acid-reacting microencapsulated compounds can be used, in which case these compounds can either be mixed with one another in the chosen ratio and then microencapsulated together, or they can be microencapsulated separately.

The following examples are given in further description of the invention:

EXAMPLE 1

40 ml of paste dye of the formula given above for the "medium blond" color was mixed with 40 ml of a 6% hydrogen peroxide emulsion of the formula also given below, which contains 7.5% of citric acid microencapsulated in fumaric acid, resulting in a hair dye with a pH of 9.5. The dye was applied to the regrowth of a previously dyed hair containing about 50% gray, and allowed to act thereon.

15 minutes after the application ended, the fumaric acid capsules had dissolved and the pH of the dye had changed from 9.5 to 7.0. After this 15-minute period the color composition, now reacting neutral to weakly acid, is combed into the lengths and ends of the hair.

The color composition was allowed to act there for 10 to 15 minutes and then shampooed out.

As a result, a uniform medium-blond color was obtained.

The gray hair at the roots was completely covered, and the length and ends of the hair looked well cared for, as manifested by its sheen and soft feel.

EXAMPLE 1

| Formula for Medium Blond Paste Dye | |
| --- | --- |
| Cetyl stearyl alcohol | 10.00 g |
| Coconut fatty acid monoethanolamide | 2.00 g |
| Stearic acid monoethanolamide | 2.00 g |
| Stearic acid diethanolamide | 1.00 g |
| p-Toluylene diamine sulfate | 0.50 g |
| Resorcinol | 0.10 g |
| 4-Chlororesorcinol | 0.10 g |
| m-Aminophenol | 0.02 g |
| Monoethanolamine | 7.00 g |
| Ammonium chloride | 0.50 g |
| Perfume | 0.30 g |
| Demineralized water to make | 100.00 g |
| Formula for $H_2O_2$ Emulsion | |
| Hydroxyethyl cellulose | 0.50 g |
| o-Phosphoric acid 85% | 0.19 g |
| Hydrogen peroxide 50%, stabilized | 12.00 g |
| Citric acid microencapsulated in fumaric acid | 7.5 g |
| Demineralized water to make | 100.00 g |

EXAMPLE 2

40 ml of dye paste of the formula given below for a "medium blond" color were mixed with 40 ml of a 6% hydrogen peroxide emulsion of the formula also given below, which contains 17.5% of carboxyl group containing an acrylic resin (Rohagit S env) encapsulated in cellulose acetate phthalate, resulting in a hair dye having a pH of 9.5. The dye was applied to the regrowth of a previously dyed hair with about 50% gray and allowed to act on it.

15 minutes after application was completed the cellulose acetate phthalate capsules had dissolved and the pH of the hair dye had changed from 9.5 to 7.0, which was also indicated visually by a darkening of the dye composition. After these 15 minutes the now neutral- to weakly acid-reacting dye composition was combed into the hair lengths and ends.

The dye composition was allowed to act there for 10 to 15 minutes and was then shampooed out.

As the result, a uniform medium blond shade was obtained.

The gray hair at the roots was completely covered, and the length and ends of the hair had a well-cared-for appearance due to its sheen and soft feel.

EXAMPLE 2

| Formula for Medium Blond Paste Dye | |
| --- | --- |
| Cetyl stearyl alcohol | 10.00 g |
| Coconut fatty acid monoethanolamide | 2.00 g |
| Stearic acid monoethanolamide | 2.00 g |
| Stearic acid diethanolamide | 1.00 g |
| p-Toluylene diamine sulfate | 0.50 g |
| Resorcinol | 0.10 g |
| 4-Chlororesorcinol | 0.10 g |
| m-Aminophenol | 0.02 g |
| Monoethanolamine | 7.00 g |
| Ammonium chloride | 0.50 g |
| Perfume | 0.30 g |
| Demineralized water to make | 100.00 g |
| Formula for $H_2O_2$ Emulsion | |
| Hydroxyethylcellulose | 0.50 g |
| o-Phosphoric acid 85% | 0.19 g |
| Hydrogen peroxide 50%, stabilized | 12.00 g |
| Acrylic resin (Rohagit S) containing carboxyl groups and microencapsulated in cellulose acetate phthalate | 17.50 g |
| Demineralized water to make | 100.00 g |

EXAMPLE 3

40 ml of paste dye of the formula given below for a "hazelnut blond" color was mixed with 40 ml of a 6% hydrogen peroxide emulsion of the formula also given below, which contains 7.5% citric acid microencapsulated in fumaric acid, resulting in a hair dye with a pH of 9.5. The dye was applied to the regrowth of an already dyed, approximately 30% gray hair and allowed to act on it.

15 minutes after completion of the application the fumaric acid capsules had dissolved and the pH of the hair dye had changed from 9.5 to 7.0. After these 15 minutes the now neutral- to weakly acid-reacting color composition was combed into the hair lengths and ends.

The color composition was here allowed to act for 10 to 15 minutes and then shampooed out.

As the result a uniform hazelnut blond color shade was obtained.

The gray hair was completely covered at the root, the length and ends of the hair appeared well cared for, as manifested by its sheen and soft feel.

EXAMPLE 3

| Formula for Hazelnut Blond Paste Dye | |
| --- | --- |
| Cetylstearyl alcohol | 10.00 g |
| Coconut fatty acid monoethanol amide | 2.00 g |
| Stearic acid monoethanol amide | 2.00 g |
| Stearic acid diethanol amide | 1.00 g |
| p-Toluylene diamine sulfate | 0.45 g |
| Resorcinol | 0.10 g |
| m-Aminophenol | 0.05 g |
| 4-Nitro-2-aminophenol | 0.05 g |
| p-Aminophenol | 0.30 g |
| p-Amino-o-cresol | 0.05 g |
| 2-Methyl resorcinol | 0.10 g |
| Ammonia 25% | 7.50 g |
| Sodium sulfite | 1.00 g |
| Ethylene diamine tetraacetic acid | 0.60 g |

-continued

| | |
|---|---|
| Ammonium chloride | 0.50 g |
| Perfume | 0.30 g |
| Demineralized water to make | 100.00 g |

| Formula for Hydrogen Peroxide Emulsion | |
|---|---|
| Hydroxyethylcellulose | 0.50 g |
| o-Phosphoric acid 85% | 0.19 g |
| Hydrogen peroxide 50%, stabilized | 12.00 g |
| Citric acid microencapsulated in fumaric acid | 7.5 g |
| Demineralized water to make | 100.00 g |

EXAMPLE 4

40 ml of paste dye of the formula given below for a "hazelnut blond" color was mixed with 40 ml of a 6% hydrogen peroxide emulsion of the formula also given below containing 17.5% of acrylic resin (Rohagit S env) microencapsulated in cellulose acetate phthalate, resulting in a hair dye with a pH of 9.5. The dye was applied to the regrowth of an already dyed hair about 30% gray and allowed to act on it.

15 minutes after completion of the application of the cellulose acetate phthalate capsules had dissolved and the pH of the dye had changed from 9.5 to 7.0, which was indicated visually by a darkening of the dye composition. After these 15 minutes the new weakly neutral- to weakly acid-reacting color composition was combed into the body and ends of the hair.

The dye composition was allowed to act there for 10 to 15 minutes and then shampooed out.

As the result a uniform hazelnut blond shade was obtained.

The gray hair was completely covered at the root, and the length and ends of the hair had a well-cared-for appearance due to its sheen and soft feel.

EXAMPLE 4

| Formula for Hazelnut Blond Paste Dye | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| p-Toluylene diamine sulfate | 0.45 g |
| Resorcinol | 0.10 g |
| m-Aminophenol | 0.05 g |
| 4-Nitro-2-aminophenol | 0.05 g |
| p-Aminophenol | 0.30 g |
| p-Amino-o-cresol | 0.05 g |
| 2-Methylresorcinol | 0.10 g |
| Ammonia 25% | 7.50 g |
| Sodium sulfite | 1.00 g |
| Ethylenediamine tetraacetic acid | 0.60 g |
| Ammonium chloride | 0.50 g |
| Perfume | 0.30 g |
| Demineralized water to make | 100.00 g |

| Formula for Hydrogen Peroxide Emulsion | |
|---|---|
| Hydroxyethylcellulose | 0.50 g |
| Orthophosphoric acid 85% | 0.19 g |
| Hydrogen peroxide 50%, stabilized | 12.00 g |
| Acrylic resin containing carboxyl groups, microencapsulated in cellulose acetate phthalate (Rohagit S) | 17.50 g |
| Demineralized water to make | 100.00 g |

EXAMPLE 5

20 grams of powder dye of the formula given below for the "dark blond" color were mixed with 40 ml of a 6% hydrogen peroxide emulsion of the formula also given below, containing 7.5% citric acid microencapsulated in fumaric acid, resulting in a hair dye with a pH of 9.5. The dye was applied to the regrowth of an already-dyed, about 30% grayed hair and allowed to act.

15 minutes after application was completed the fumaric acid capsules had dissolved and the pH of the hair dye had changes from 9.5 to 7.0, which was also indicated visually by a darkening of the dye substance. After these 15 minutes the dye substance, which now had a neutral to slightly acid reaction, was combed into the body and tips of the hair.

The dye was allowed to act there for 10 to 15 minutes and then shampooed out.

As a result, a uniform dark blond shade of color was obtained.

The gray hair was completely covered at the roots, the body and tips of the hair had a well-cared-for appearance as indicated by the sheen and soft feel.

EXAMPLE 5

| Formula for Dark Blond Dye Powder | |
|---|---|
| Hydroxyethylcellulose | 2.00 g |
| Sodium metasilicate | 6.00 g |
| Silicon dioxide (Aerosil) | 90.10 g |
| Ethylenediamine tetraacetic acid | 0.60 g |
| Ammonium chloride | 0.50 g |
| p-Toluylenediamine sulfate microencapsulated in gelatine | 0.50 g |
| Resorcinol | 0.20 g |
| m-Aminophenol microencapsulated in gelatine | 0.10 g |
| | 100.00 g |

| Formula for Hydrogen Peroxide Emulsion | |
|---|---|
| Hydroxyethylcellulose | 0.50 g |
| o-Phosphoric acid 85% | 0.19 g |
| Hydrogen peroxide 50%, stabilized | 12.00 g |
| Citric acid encapsulated in fumaric acid | 7.50 g |
| Demineralized water to make | 100.00 g |

EXAMPLE 6

20 g of dye powder of the formula given below for the "Dark Blond" dye was mixed with 40 ml of water; the immediate dissolution of the gelatine capsules resulted in a hair dye with a pH of 9.5. The dye was applied to the regrowth of a previously dyed, about 30% gray, hair and allowed to act.

15 minutes after completion of the application the fumaric acid capsules had dissolved and the pH of the hair dye had changes from 9.5 to 7.0, indicated visually by a darkening of the dye substance. After these 15 minutes the new neutral to weakly acid-reacting dye was combed into the body and ends of the hair.

The dye was allowed to act there for 10–15 minutes and then shampooed out.

As a result, a uniform dark blond shade was obtained.

The gray hair at the roots was completely covered, and the body and ends of the hair had a well-cared-for look indicated by its sheen and soft feel.

EXAMPLE 6

| Formula for Dark Blond Powder Dye | |
|---|---|
| Hydroxyethylcellulose | 2.00 g |
| Sodium metasilicate | 6.00 g |
| Silicon dioxide (Aerosil) | 72.60 g |
| Ethylenediamine tetraacetic acid | 0.60 g |
| Ammonium chloride | 0.50 g |
| Resorcinol | 0.20 g |
| p-Toluenediamine sulfate microencapsulated in gelatine | 0.50 g |

-continued

| Formula for Dark Blond Powder Dye | |
| --- | --- |
| m-Aminophenol microencapsulated in gelatine | 0.10 g |
| Urea peroxide microencapsulated in gelatine | 10.00 g |
| Citric acid microencapsulated in fumaric acid | 7.50 g |
| | 100.00 g |

EXAMPLE 7

40 ml of paste dye of the formula given below for the "Medium Blond" dye was mixed with 40 ml of a 6% hydrogen peroxide emulsion of the formula also given below, resulting in a hair dye with a pH of 9.5. To this was added 3.2 g of a microencapsulated citric acid whose wall material consisted of copolymers of acrylic acid and methacrylic acid esters, such as, for example, Eudragit L30D and Eudragit RS30D. The weight ratio of wall material to core material was selected at 30 to 70. The dye was applied to the regrowth of a previously dyed, about 50% gray, hair and allowed to act.

15 minutes after completion of the application the entire dye substance was combed into the body and ends of the hair. Due to the mechanical friction of the combing, the capsule walls, having softened in the dye, were destroyed and the pH of the dye changed from 9.5 to pH 6.8.

The dye was allowed to act there for 15 minutes and then shampooed out.

As a result a uniform medium blond shade was obtained.

The gray hair at the root was completely covered, and the body and ends of the hair had a well-cared-for appearance manifested by its sheen and soft feel.

EXAMPLE 7

| Formula for Medium Blond Paste Dye | |
| --- | --- |
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| p-Toluylenediamine sulfate | 0.50 g |
| Resorcinol | 0.10 g |
| 4-Chlororesorcinol | 0.10 g |
| m-Aminophenol | 0.02 g |
| Monoethanolamine | 7.00 g |
| Ammonium chloride | 0.50 g |
| Perfume | 0.30 g |
| Demineralized water to make | 100.00 g |
| Formula for Hydrogen Peroxide Emulsion | |
| Hydroxyethylcellulose | 0.50 g |
| Orthophosphoric acid 85% | 0.19 g |
| Hydrogen peroxide 50%, stabilized | 12.00 g |
| Demineralized water to make | 100.00 g |

EXAMPLE 8

40 ml of paste dye of the formula given below for the "Medium Blond" dye was mixed with 40 ml of a 6% hydrogen peroxide emulsion of the formula also given below, resulting in a hair dye with a pH of 9.5. To this was added 3.2 g of a microencapsulated ascorbic acid whose wall material consisted of copolymers of acrylic acid and methacrylic acid esters, such as, for example, Eudragit L30D and Eudragit RS30D. The wall material amounted to 30% of the weight of the microcapsules. The dye was applied to the regrowth of a previously dyed, about 50% gray, hair and allowed to act.

15 minutes after completion of the application the entire dye substance was combed into the body and ends of the hair. Due to the mechanical friction of the combing, the capsule walls, having softened in the dye, were destroyed and the pH of the dye changed from 9.5 to pH 7.1. The temperature of the dye rose from 25° C. to 38° C. and the $H_2O_2$ content of the dye decreased from 1.92% to 1.50%.

The dye was allowed to act here for 8 minutes and then shampooed out.

As a result, a uniform medium blond shade was obtained.

The gray hair at the roots was completely covered, and the body and ends of the hair had a well-cared-for look indicated by its sheen and soft feel.

EXAMPLE 8

| Formula for Medium Blond Paste Dye | |
| --- | --- |
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| p-Toluylenediamine sulfate | 0.50 g |
| Resorcinol | 0.10 g |
| 4-Chlororesorcinol | 0.10 g |
| m-Aminophenol | 0.02 g |
| Monoethanolamine | 7.00 g |
| Ammonium chloride | 0.50 g |
| Perfume | 0.30 g |
| Demineralized water to make | 100.00 g |
| Formula for $H_2O_2$ Emulsion | |
| Hydroxyethyl cellulose | 0.50 g |
| Orthophosphoric acid 85% | 0.19 g |
| Hydrogen peroxide 50%, stabilized | 12.00 g |
| Demineralized water to make | 100.00 g |

We claim:

1. A composition for the oxidative dyeing of human or animal hair, prepared immediately before application to hair, comprising:
    a mixture of an oxidant and at least one oxidative dye in an alkaline cream, gel or powder base having a pH between 8.0 to 10.5,
    an acid encapsulated into microcapsules, said microcapsules being soluble in an alkaline environment such that within 10 to 60 minutes said microcapsules dissolve in said mixture or can be mechanically broken as by combing, and the acid is released into the mixture wherein said acid reacts with said alkaline cream, gel or powder base to change the pH of the mixture to a weakly alkaline (pH≦8), neutral or mildly acidic range.

2. The composition according to claim 1, wherein the acid is selected from the group consisting of citric acid, tartaric acid, malic acid, and ascorbic acid.

3. The composition according to claim 1, wherein the acid is an acrylic resin containing carboxyl groups.

4. The composition according to claim 2, wherein the acid includes an indicator which causes a color change upon mixing with said alkaline cream, gel, or powder base.

5. The composition according to claim 1, wherein the microcapsules are made of fumaric acid whenever the acid is citric acid, cellulose acetate phthalate whenever the acid is an acrylic resin containing carboxyl groups, and copolymers of acrylic acid or methacrylic acid esters whenever the acid is ascorbic acid.

6. A method of preparing an agent for oxidative dyeing of human or animal hair, comprising the steps of:
mixing an oxidant with an alkaline cream, gel or powder base having a pH between 8.0 and 10.5 containing at least one oxidative dye, and microcapsules containing an acid, said microcapsules being soluble in said alkaline cream, gel or powder base or capable of being mechanically broken as by combing, such that within 10 to 60 minutes the acid is released into the mixture to lower the pH of the mixture to a weakly alkaline (pH≦8), neutral or mildly acidic range.

7. A method of dyeing human or animal hair, comprising the steps of:
preparing a dyeing agent having a pH which is weakly alkaline, neutral or in a mildly acidic range by mixing an oxidant, an alkaline cream, gel or powder base containing an effective amount of oxidative dye having a pH adjusted between 0.8 to 10.5 with an acid encapsulated into microcapsules soluble in an alkaline environment such that within 10 to 60 minutes the microcapsules dissolve or may be broken by combing, the acid being released thereby into the mixture, changing the pH of the mixture to a weakly alkaline (pH≦8), neutral or mildly acidic range; immediately applying the dyeing agent to the hair and letting the same act for an effective period of time sufficient to dye the hair; washing the dyeing agent out of the hair.

8. A method of redyeing human or animal hair, comprising the steps of:
preparing a dyeing agent having a pH which is weakly alkaline, neutral or in a mildly acidic range by mixing of an oxidant, an alkaline cream, gel or powder base containing an effective amount of an oxidative dye having a pH adjusted between 8.0 to 10.5, and an acid encapsulated into microcapsules soluble in an alkaline environment such that within 10 to 60 minutes the microcapsules dissolve or may be broken as by combing, said acid being released thereby into the mixture rendering the pH of the mixture to a weakly alkaline (pH≦8), neutral or mildly acidic range; applying the dyeing agent to recent growth of hair until the microcapsules have dissolved and the pH of said base has changed to a weakly alkaline, neutral or mildly acidic range; combing the dyeing agent into the hair; letting the dyeing agent act for a period of time sufficient to dye recent growth of hair; washing the dyeing agent out of the hair.

9. A method of redyeing human or animal hair according to claim 4 wherein the alkaline cream, gel or powder base containing at least one oxidative dye, the oxidant, the microencapsulated acid are kept in separate stocks and are mixed together immediately before the preparation of the dyeing agent for application to human hair.

* * * * *